United States Patent
Ekey (12)

(10) Patent No.: US 6,270,485 B1
(45) Date of Patent: Aug. 7, 2001

(54) POST SURGICAL DRAIN RECEPTACLE SUPPORT SYSTEM

(76) Inventor: Barbara Norton Ekey, 393 Keller Rd., Warren, PA (US) 16365

( * ) Notice: Subject to any disclaimer, the term of this patent is extended or adjusted under 35 U.S.C. 154(b) by 0 days.

(21) Appl. No.: 09/288,181

(22) Filed: Apr. 8, 1999

Related U.S. Application Data

(63) Continuation-in-part of application No. 09/092,602, filed on Jun. 5, 1998, now Pat. No. 5,980,499.

(51) Int. Cl.$^7$ ........................................... A61F 5/449
(52) U.S. Cl. .................. 604/345; 604/327; 604/332; 604/174; 604/179; 224/224; 224/226; 224/252; 224/253; 224/663; 224/676
(58) Field of Search ..................... 604/174, 317, 604/349, 180, 682, 179, 347, 332, 327, 353, 346, 345, 337; 224/252, 253, 224, 226, 676, 663

(56) References Cited

U.S. PATENT DOCUMENTS

| | | | |
|---|---|---|---|
| D. 128,066 | 7/1941 | Haubein . | |
| D. 277,810 | 3/1985 | Pickens | D2/383 |
| D. 319,732 | 9/1991 | Gums | D3/100 |
| D. 365,928 | 1/1996 | Sauer | D3/224 |
| 1,382,446 | * 6/1921 | Warren . | |
| 1,968,767 | 7/1934 | Howard | 221/23 |
| 2,699,782 | 1/1955 | Chester | 128/295 |
| 2,900,979 | 8/1959 | Bishop . | |
| 3,919,615 | * 11/1975 | Nieck | 320/2 |
| 4,122,851 | * 10/1978 | Grossner | 128/295 |
| 4,411,267 | * 10/1983 | Heyman | 128/385 |
| 4,435,171 | * 3/1984 | Goldberg | 604/49 |
| 4,504,267 | * 3/1985 | Parmelee | 604/134 |
| 4,548,375 | 10/1985 | Moss | 248/205.2 |
| 4,620,653 | * 11/1986 | Farrell | 224/242 |
| 4,747,527 | * 5/1988 | Trumpower | 224/224 |

(List continued on next page.)

FOREIGN PATENT DOCUMENTS 76 09199 * 3/1976 (FR) ........................................... 5/44

OTHER PUBLICATIONS

Author unknown, "New Kits Help Patients manage Fluid Drainage after Lumpectomy, masectomy, and Breast Reconstruction," Jan. 13, 2000, http://www.imaginis. com.*

*Primary Examiner*—John G. Weiss
*Assistant Examiner*—Michael Bogart
(74) *Attorney, Agent, or Firm*—Thompson Hine LLP

(57) ABSTRACT

A drainage receptacle support system for use by a postoperative patient. The support device includes an adjustable belt and a plurality of pouches for individually receiving a drainage receptacle. A loop is provided on the back of the pouch for slidably receiving the belt, so that the pouch may be positioned directly underneath or directly above an insertion point for the drainage tubes. The loop is positioned so that the pockets are held in a generally upright position. Preferably the support device is lightweight and washable, and the pockets and the loop include padding to distribute the weight of the receptacle. Additionally, a releasable hinge is provided to secure excess slack from a drainage tube to the body of a wearer and gussets are used to accommodate larger drainage receptacles in pockets, and elongated pouches with two security hinges accommodate narrow drains with valves in the middle of the tubing.

17 Claims, 6 Drawing Sheets

U.S. PATENT DOCUMENTS

| | | | | |
|---|---|---|---|---|
| 4,819,846 | * | 4/1989 | Hannenman | 224/240 |
| 4,923,105 | * | 5/1990 | Snyder | 224/255 |
| 4,957,231 | * | 9/1990 | Kalisher | 224/151 |
| 5,026,362 | | 6/1991 | Willett | 604/345 |
| 5,032,118 | | 7/1991 | Mason | 604/349 |
| 5,087,251 | | 2/1992 | Heyman et al. | |
| 5,135,519 | | 8/1992 | Helmer | 604/332 |
| 5,188,587 | * | 2/1993 | McGuire | 602/20 |
| 5,211,321 | * | 5/1993 | Rodriguez | 224/215 |
| 5,237,988 | * | 8/1993 | McNeese | 128/207.17 |
| 5,259,541 | | 11/1993 | Reese | 224/226 |
| 5,395,022 | * | 3/1995 | Vandewall | 224/226 |
| 5,496,282 | * | 3/1996 | Militzer | 604/179 |
| 5,590,760 | * | 1/1997 | Astarb | 206/6 |
| 5,643,233 | | 7/1997 | Turner | 604/332 |
| 5,651,777 | | 7/1997 | Walters | 604/345 |
| 5,716,344 | | 2/1998 | Kiel | 604/174 |
| 5,728,070 | * | 3/1998 | Walker | 604/179 |
| 5,776,105 | * | 7/1998 | Corn | 604/174 |
| 5,836,497 | * | 11/1998 | Pelish | 224/677 |
| 5,964,386 | * | 10/1999 | Cote | 224/250 |

* cited by examiner

POST SURGICAL DRAIN RECEPTACLE SUPPORT SYSTEM

CROSS REFERENCE TO RELATED APPLICATION

This application is a continuation-in-part of U.S. Ser. No. 09/092,602 filed Jun. 5, 1998, now U.S. Pat. No. 5,980,499.

BACKGROUND OF THE INVENTION

This invention relates to post surgical drain receptacle supports, and more particularly to drain receptacle supports to be worn about the abdomen, thorax, upper thigh or head.

Following certain types of surgery, especially surgery involving the removal of tissue, the resulting body cavity may fill with fluid. Examples of such surgery include mastectomies and lumpectomies with auxiliary nodal dissection involving removal of lymph nodes under the arm, various transplants and reconstruction. The removal of the large amount of tissue in such procedures creates a cavity, and as a result, the remaining lymph nodes secrete fluid which collects in the cavity. To relieve swelling and infection that may occur if the fluid is left in the body, a drainage tube is inserted through the surgical incision into the cavity. Such drain tubes typically have perforated ends through which fluid enters the tube from the cavity. Drainage of such fluid provides the further advantage of creating a negative pressure in the body cavity, thereby holding the skin against the muscle until it heals. When such operations require tissue removal from multiple sites, postoperative treatment will utilize multiple tubes and bottles, each associated with a separate incision.

The drainage tubes connect to receptacles, such as plastic bottles, for collecting the fluid. Depending on the surgery and the amount of fluid buildup expected, the number of drainage tubes and receptacles utilized can vary from as few as one to as many as four. In addition, the size and shape of the respective receptacles can also vary. For example, for some neck and head surgeries, larger drainage bottles, having flat front and back surfaces may be used; for certain facial surgeries a small, test tube like drain is used; for heart and thoracic surgeries a long drain valve with a receptacle is used; while for other surgeries the standard medium sized, rounded receptacles are satisfactory. Notwithstanding the shape, size and number of receptacles used, managing the tubes and monitoring fluid collection in their associated receptacles generally pose certain problems in that receptacles need to be supported in some way and that the tubes become entangled with the wearer, the wearer's clothes, etc.

In the past, it was common to pin or tape the receptacles to clothing worn by the patient or to the bandage or the incision itself. While not very comfortable, this procedure was somewhat effective in the hospital where an open gown was worn, thereby easing the ability of the patient to accommodate basic bodily function. Furthermore, the awkwardness and discomfort is increased with multiple sets of bottles and tubes. In addition, outside the hospital, where patients wear standard, relatively constricting clothes, it is not practicable to use such means to receive drain bottles. As mentioned above, other problems arise from the entanglement of the tubes themselves. For example, the drainage tubes are generally connected to the drainage bottles with an ample amount of "slack" so that they will be usable in varying application by patients of differing sizes and shapes. However, the extra length of the tubes can become easily entangled with the wearer, the wearer's clothing, etc., especially when several drainage bottles are being used. Thus, with the advent of insurance company mandates on shorter hospital stays for many types of surgeries, these types of problems have become more prevalent.

U.S. Pat. No. 5,643,233 to Turner attempts to address some of these problems by providing a single large pouch to be worn on a belt which extends about the waist of a post operative patient to support a fluid drainage receptacle. The pouch of that device includes a pouch extension and an elongated loop of fabric which receives the belt and supports the pouch so that the pouch opening hangs down below the belt and deflects in an angular position when the lip of the pouch is pulled away from the wearer, thereby allowing easy access to the interior of the pouch.

While the Turner patent resolves some of the problems associated with prior art post operative drainage receptacle supports, it is not completely effective. For example, the Turner device cannot hold a number of drainage receptacles individually in separate, secured upright positions about a patient's body in locations which avoid tangling of the drainage bottles. Also, the Turner device is not compatible for use with the larger, flat sided receptacles or for the elongated drain valves with receptacles that are used after certain surgical procedures and does not address the problems associated with securing excess slack from long drainage tubes to avoid entanglements.

Accordingly, there exists a need for a lightweight support device for drainage receptacle to be worn by post operative patients which comfortably secures the drainage receptacle against a wearer, a support device which can be worn under clothing, a support device which facilitates draining of receptacles, a support device which prevents tube entanglements, a support device which holds the drain upright, a support device which may be used with receptacles of varying sizes and shapes, and a support device which can be positioned in a manner to avoid tangling and stress on the drain tubes.

SUMMARY OF THE INVENTION

The present invention is a post surgical drain receptacle support system which securely supports a number of drainage receptacles and can be worn comfortably by a postoperative patient. The present invention includes an adjustable belt and at least one pouch shaped to receive an individual drain receptacle, typically a plastic bottle, and includes a loop for receiving the adjustable belt. The pouch may be constructed in many different ways, but in a preferred embodiment it includes a side panel or gusset so that it may comfortably receive larger sized receptacles or with two security hinges for an upper drain valve and a narrower pouch for tube-like receptacle. The pouch preferably is positioned on the belt directly underneath or above the point of insertion for the drainage tube in the incision, thereby minimizing stretching of the tube, stressing the incision and the chance of entanglement with another tube. The lip of the cavity of the pocket is held at least even with the belt, thereby securing the pocket close to the body of the wearer. Preferably, the pouch of the present invention is made from a lightweight, non-abrasive, washable fabric having padding positioned between the bottle and the body of the wearer. In a preferred embodiment, a flap of fabric, or other suitable material, is affixed to the front of the pocket. The flap is secured to the pocket to form a hinge and includes one element of a releasable closure, such as a snap, a button, strips of hook and loop material or the like, affixed to the free end of the "hinge." The other element of the releasable closure is then affixed to the front of the pouch thereby enabling the flap to form a loop when the flap is releasably fastened to the front of the pouch. The loop can then be used to retain excess slack from the drainage tube, thereby lessening the possibility that the tube will become entangled with the wearer, door handles or other objects.

If a number of incisions are made in an operation, the system can be expanded to accommodate a number of pouches, each individually positioned on the belt and corresponding to a like number of drainage bottles. Such a system can be adjusted easily by a patient.

Accordingly, it is an objective of the present invention to provide a support system for post operative drainage receptacles to be worn by patients which individually supports the drainage receptacles in an upright position against the body to avoid the tangling and stretching of the drainage tubes; a system which can be adapted to support a number of drainage receptacles of varying sizes and shapes; a system which includes a device for retaining excess slack from the drainage tubes; a system which facilitates the drainage of incisions into receptacles; a system which facilitates the monitoring of fluids collected, and a system which can be worn under clothing, and is lightweight, washable and comfortable.

Other objects and advantages of the present invention will be apparent from the following description, the accompanying drawing and the appended claims.

DETAILED DESCRIPTION

Figure 1:
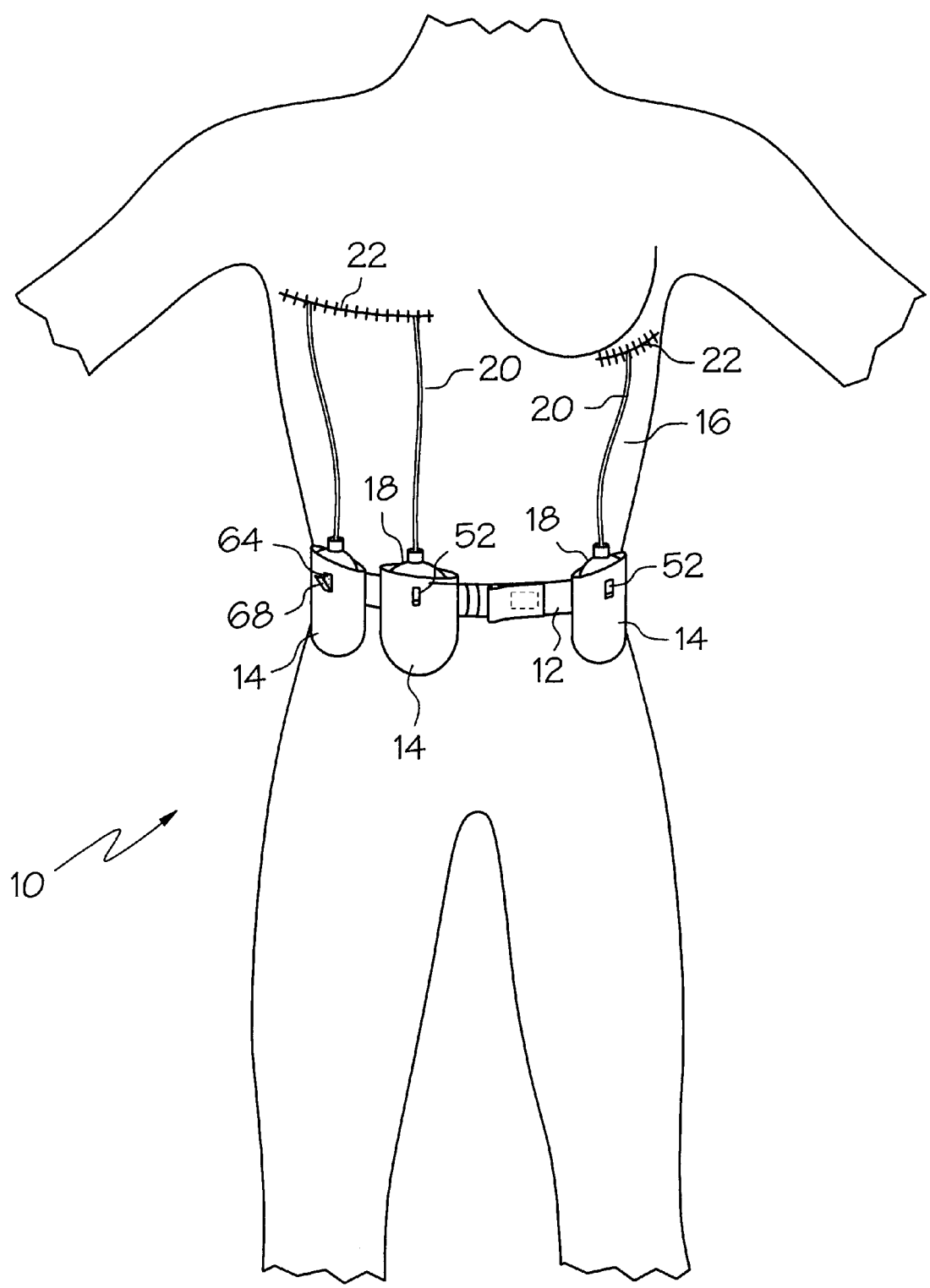
FIG. 1 is a front perspective view of the drainage receptacle support system of the present invention, shown worn by a postoperative patient.

As shown in FIG. 1, in accordance with a preferred embodiment of the present invention, a support system for a fluid drainage receptacle, generally designated 10, includes an adjustable belt 12 and a plurality of pockets 14. The belt 12 is shaped to be worn around the abdomen, thorax, head or upper thigh of a patient 16. While a human patient 16 is shown in FIG. 1, the system 10 may be employed on animals, such as horses and cows as well, and therefore are to be included with the term "Patient" as used herein. The pockets 14 are shaped to slidably receive an adjustable belt 12 and to receive an individual drainage receptacle, such as a plastic bottle 18. Drainage tubes 20 are inserted in incision 22 on a patient 16 and extend downwardly into bottles 18.

Figure 2:
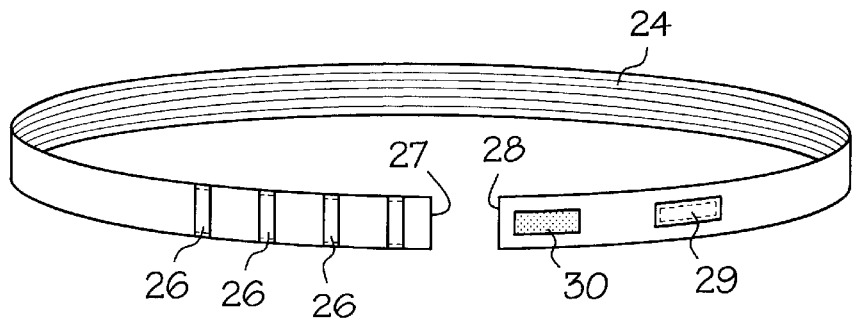
FIG. 2 is a front perspective view of the belt of the support system of FIG. 1.

As shown in FIG. 2, the adjustable belt 12 preferably is made from an elastic fabric material and has a non-abrasive facing 24 attached to the inside portion facing the wearer. Fabric adjustment loops 26 are attached to the outside of one end 27 of the belt 12 in a spaced array. Complementary strips 29, 30 of hook and loop material are attached to the opposite end 28 of the belt 12 spaced a distance apart from each other.

Figure 3:
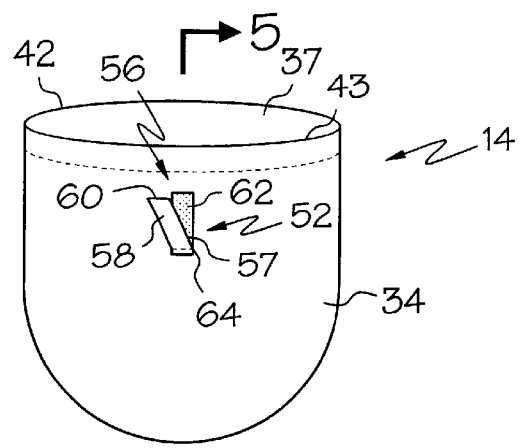
FIG. 3 is a front perspective view of the pocket of the support system of FIG. 1.
Figure 4:
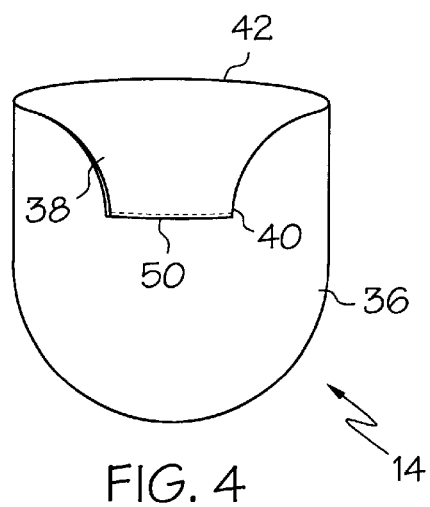
FIG. 4 is a rear perspective view of the pocket of the support system of FIG. 1.
Figure 5:
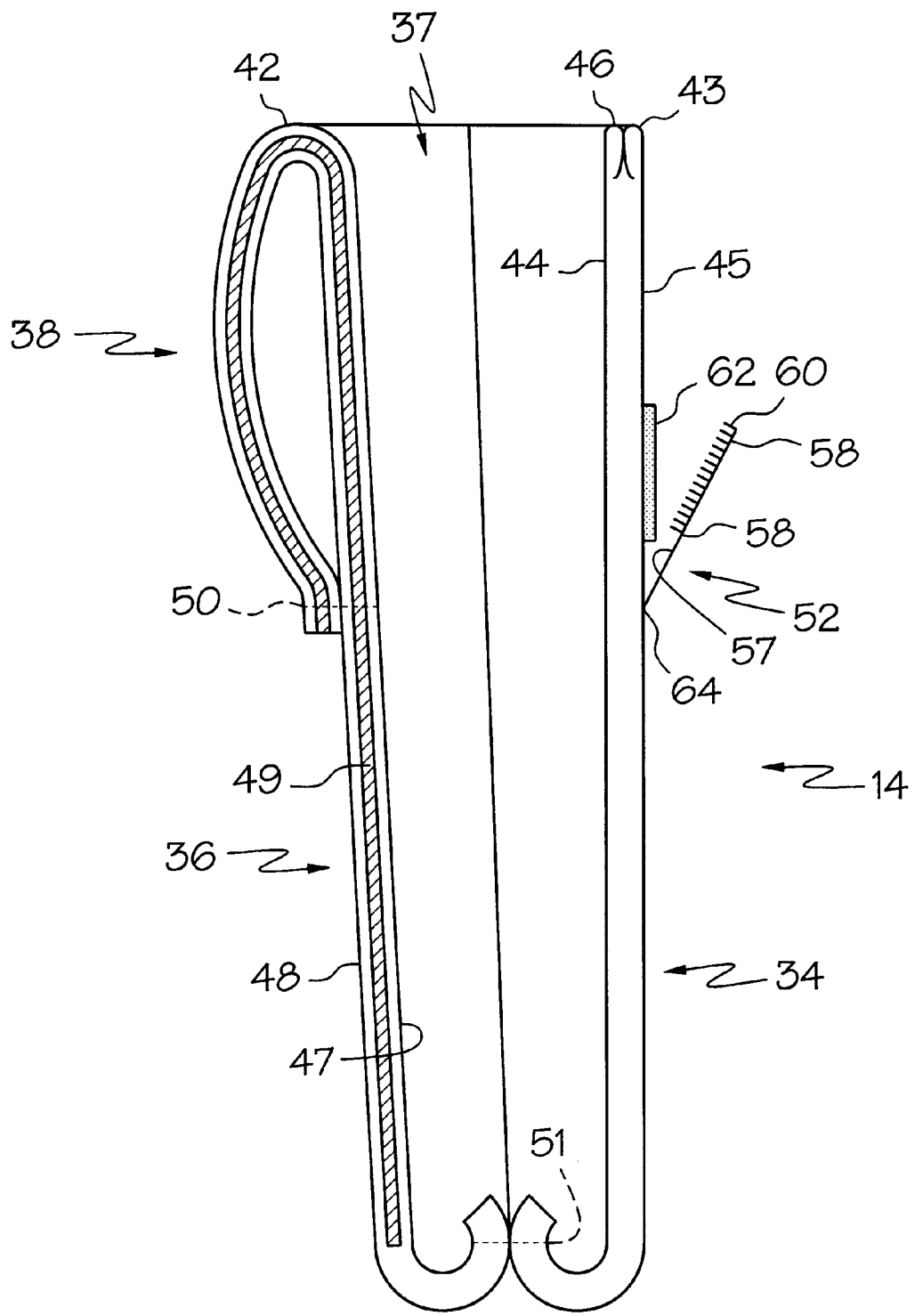
FIG. 5 is a sectional view of the pocket of the present invention, taken at line 5—5 of FIG. 3.

As shown in FIGS. 3, 4, and 5, the pocket 14 of the present invention includes a front panel 34 and a back panel 36, preferably made from a soft, non-abrasive material such as cotton. The front and back panels 34, 36 form an internal cavity 37 shaped to receive a surgical drainage receptacle 18 (see FIG. 1). The back panel 36 includes a loop 38 shaped to slidably receive the belt and is formed by turning an edge 40 of the back panel 38 over upon the back panel 36 and attaching it to itself thereby forming the loop. The top 42 of the loop is even with the top 43 of the front panel 34.

As shown in FIG. 5, the front panel 34 is made of inner and outer layers 44, 45 of fabric stitched together at 46 at the top 43. The back panel 38 includes inner and outer layers 47, 48 of fabric, which enclose a panel 44 of foam. Layer 47, 48 of fabric, and foam panel 49, fold over on themselves to form loop 38, secured by stitching 50. The front and back panels 34, 36 are joined by stitching 51 which extends about the inner position of the pocket 14.

The loop 38 is shaped to hold the pocket 14 firmly against the belt 12 such. that the belt is below or even with the top 43 of the front panel 34 (the top of the loop comprises the top of the back panel 36), thereby insuring that a receptacle 18 carried in the pocket 14 will be held in a substantially upright position. Since the pocket 14 is held firmly against the belt 12, the pocket is held firmly against the patient, which minimizes movement of the pocket relative to the patient. The foam panel 49 distributes pressure from a receptacle 18 carried in the internal cavity 32 of the pocket 14 about the back panel 36 and loop 38, thus adding to the comfort of the system 10.

Figure 6:
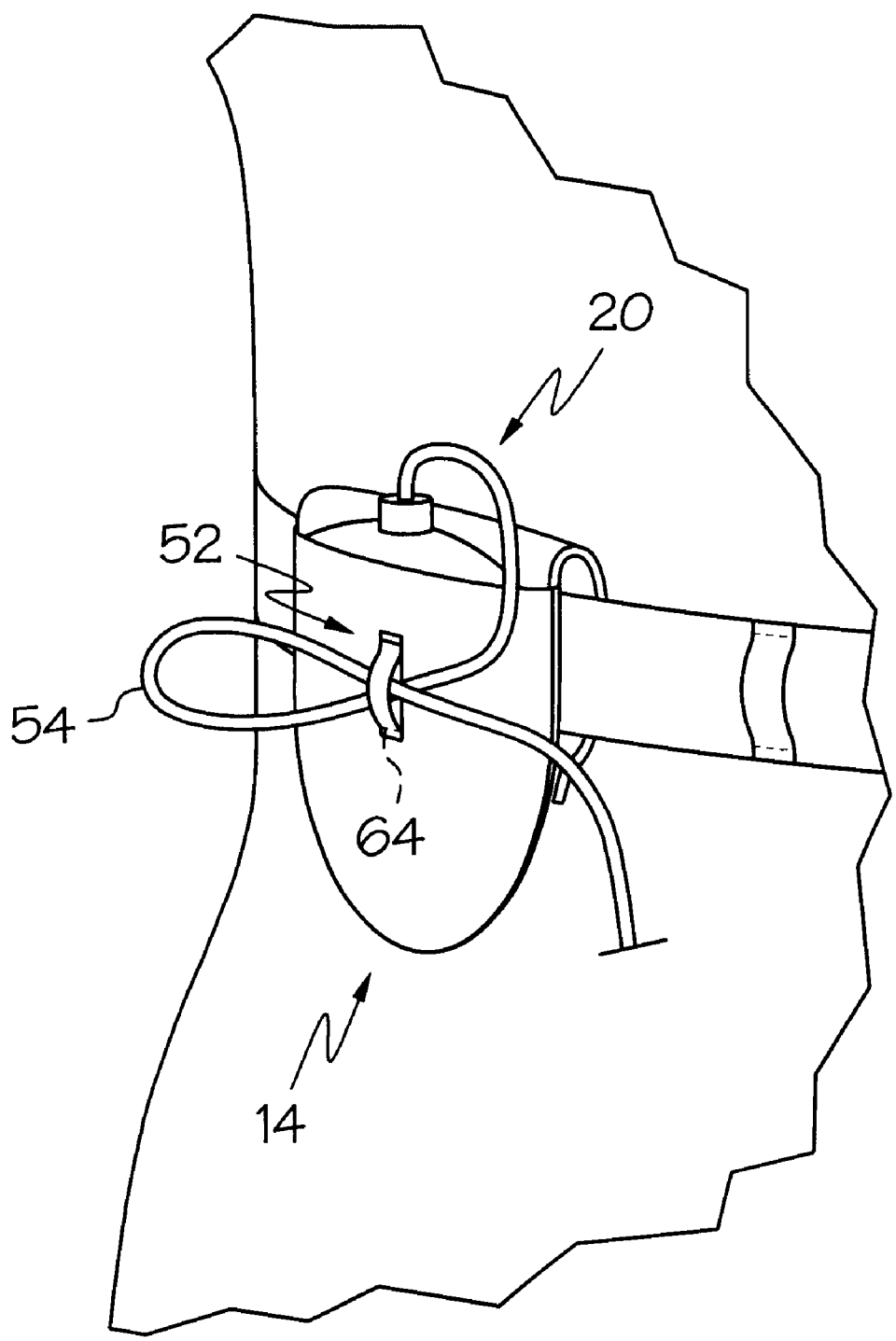
FIG. 6 is a front perspective view of the support system of FIG. 1 incorporating a tube security hinge shown on the body of a wearer.

In a preferred embodiment, as shown in FIGS. 3 and 5, a tube security hinge 52 is attached to the outer surface of the front panel 34 of the pocket 14. As best shown in FIG. 6, the hinge 52 is provided to secure excess slack 54 from the drainage tubing 20 close to the body of a wearer, thereby preventing the tubing 20 from becoming entangled with clothes, door handles, etc. The hinge 52 preferably consists of a flap of fabric 56, or other suitable material, which is affixed to the front panel 34 of the pocket 14. The flap 56 is sewn to the pocket at a fixed end 64 forming a crotch 57 and leaving a free end 58. Preferably, hook material 60 is affixed to the free end 58 of the flap 56 and loop material 62 is affixed to the front panel 34 of the pocket 14 or to the back of the fixed end 64 of the hinge 52, thereby enabling the flap 56 to form a loop when the flap is releasably fastened to the front of the pocket 14. The loop can then be used to retain excess slack 54 from the drainage tube 20, thereby lessening the possibility that the tube 20 will become entangled with the wearer, or with door handles or other objects. Of course, other releasable closures and constructions, such as snaps or buttons, may be used in connection with the security hinge 52 herein described, all of which are considered within the scope of the present invention.

Figure 7:
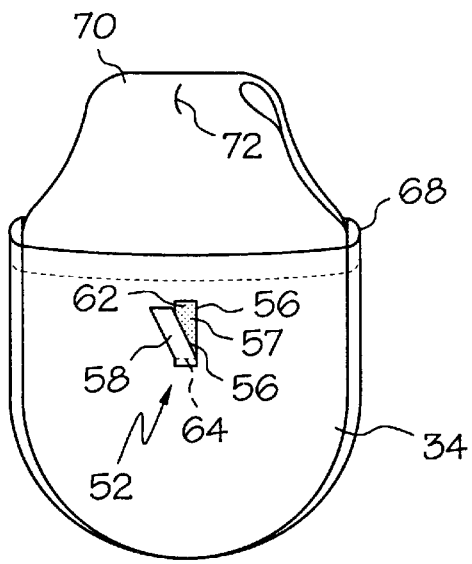
FIG. 7 is a front perspective view of an alternate embodiment of the drainage receptacle support system of the present invention employing an expansion gusset.
Figure 8:
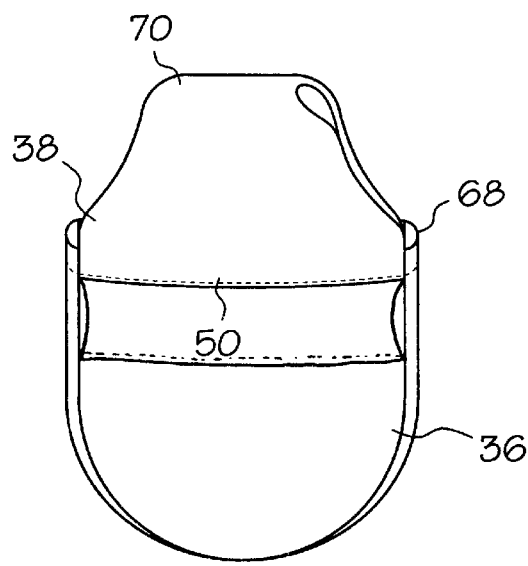
FIG. 8 is a rear perspective view of the support system of FIG. 7.
Figure 9:
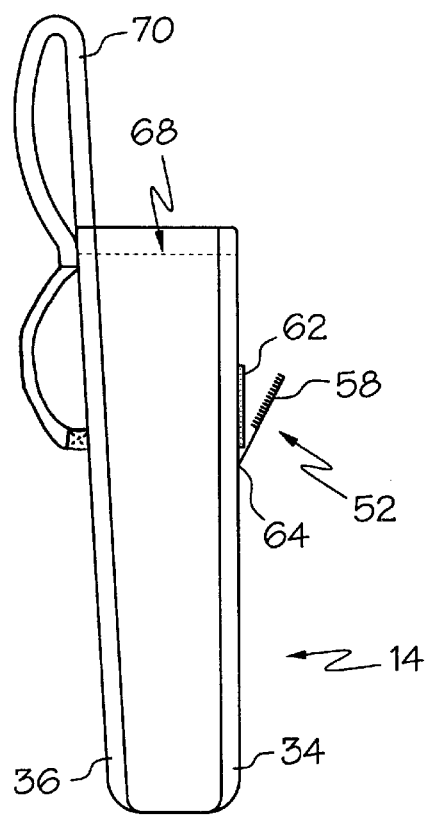
FIG. 9 is a side perspective view of the support system of FIG. 7.

Additionally, it is noted that after some neck, head and thoracic surgeries, larger drains having flat front and back surfaces are sometimes required. Accordingly, as shown in FIGS. 7, 8, and 9 in an alternate embodiment of the present invention, a gusset 68 is provided to expand the storage volume of the pocket 14. In order to accommodate these larger drainage receptacles 18, the gusset 68 is sewn in between the front and back panels 34, 36 of the pocket 14. The gusset 68 can be fabricated from a single piece of fabric, thereby expanding the pocket volume on the bottom of the pocket 14 as well as on the sides. Alternatively, the gusset 68 can be split into two separate pieces which are sewn to the front and back panels 34, 36 separately, thereby only expanding the sides of the pocket 14. In a preferred embodiment the gusset 68 is made from a material having some elastic properties so that when a drainage receptacle 18 is placed in the pocket 14, it is securely held therein.

Figure 10:
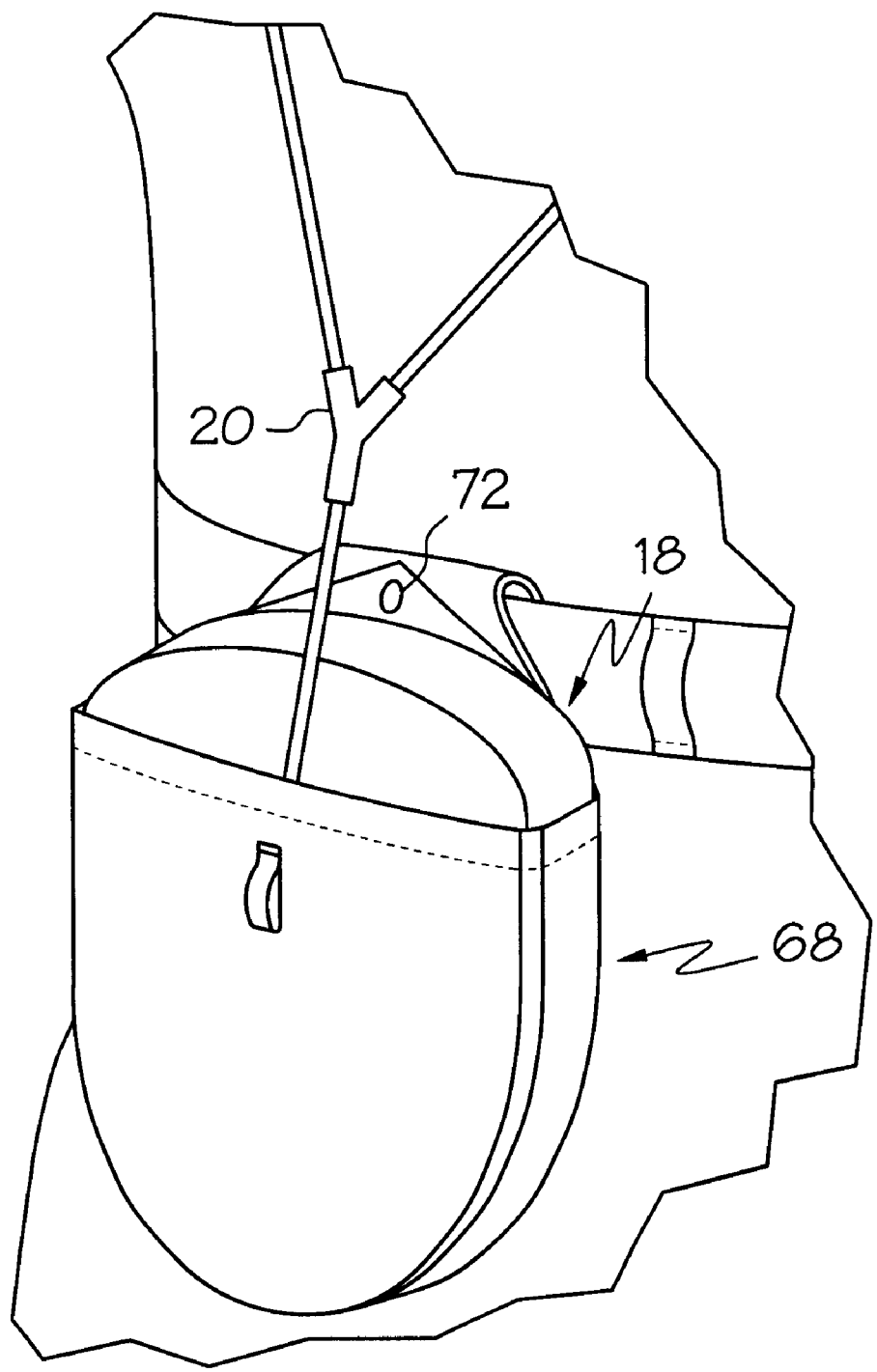
FIG. 10 is a front perspective view of the support system of FIG. 7.

Additionally, as seen best in FIG. 10, the alternate embodiment of the present invention employing a gusset 68 is also equipped with an additional support flap 70 which extends from the back panel 36 of the pocket. The additional support flap 70, which may be in the shape of a loop, is preferably equipped with a snap, hook or button 72, so that a drainage receptacle 18 may be attached to the flap 70.

The operation of the drainage receptacle support device of the present invention is as follows. A number of pockets 14 corresponding to a like number of drainage receptacles 18 are selected and slidably mounted on the belt 12. The belt 12 is then placed around the abdomen of post operative patient 16 and end 28 of the belt 12 having a hook strip 29 and a loop strip 30 of material attached thereto is fed through a selected one of the adjustment loops 26 providing the most comfortable fit for the belt 12. The end of the belt is then turned upon itself so that the complementary strips 29, 30 of hook and loop material engage each other thereby fastening the belt. Any portion of the belt 12 not being used may be cut off at one of the blue stitching next to the loop.

Next, the pockets 14 may be positioned on the belt 12 in a least restrictive, most comfortable, position for the post operative patient 16 in order to avoid tugging on and tangling of the drainage tubes 20, which typically is directly underneath each corresponding insertion point 22. Drainage receptacles 18 are each placed in an individual corresponding pocket 14 providing the postoperative patient with support in an upright position. The receptacles 14 may be easily removed for emptying, and the receptacle support device 10 may be washed as necessary.

Finally, the excess slack 54 from the drainage tubes 20 is collected and folded upon itself to form a bundle. The bundle is then placed in the crotch 57 of the security hinge 52 and the free end 58 of the hinge 52 is closed, binding the bundle of slack 54 therein. In this way the slack 54 is held close to the body of a wearer and is prevented from unwanted entanglements.

While the form of the apparatus therein described constitutes a preferred embodiment of the invention, it is to be understood that the invention is not limited to the precise form of apparatus, and that changes may be made therein without departing from the scope of the invention.

What is claimed is:

1. A support device for use with a drainage receptacle connected to a postoperative surgery patient comprising:
    a belt shaped to be worn about the abdomen, thorax, head or upper thigh of a wearer;
    a pocket having an internal cavity shaped to receive a surgical drainage receptacle, said pocket having a back panel and a front panel, said back panel made of a relatively non-abrasive material and having padding positioned therein such that pressure from a receptacle carried in said cavity is distributed about said back panel, a hinge having a fixed end and a free end and forming a crotch attached to said front panel, said free end having a closure for releasably attaching said free end to said front panel wherein said fixed end of said hinge is positioned on said front panel below said free end of said hinge such that said crotch can support excess slack from a tube connected to a surgical drainage receptacle when said free end of said hinge is attached to said front panel, wherein said back panel also includes a loop for slidably receiving said belt, said loop being shaped to hold said pocket against said belt such that said belt is below an upper surface of said back panel, wherein said pocket is held against a wearer such that a carried receptacle is held in a substantially upright position.

2. The support device of claim 1 wherein said loop is unitary with said back panel.

3. The support device of claim 1 wherein said closure for releasably attaching said hinge to said front is selected from the group consisting of hook and loop material, snaps, buttons, and clasps.

4. The support device of claim 1 wherein said closure for releasably attaching said hinge to said front is hook and loop material.

5. The support device of claim 3 wherein said front panel includes an upper edge positioned substantially even with an upper edge of said back panel.

6. The support device of claim 5 wherein said upper edges of said front and back panel define a mouth of said cavity.

7. The support device of claim 3 wherein said front panel is made of a relatively non-abrasive material.

8. The support device of claim 1 further comprising a plurality of said pockets attached to said belt.

9. The support device of claim 1 wherein said belt is made of an elastic material.

10. A support device for use with a drainage receptacle connected to a postoperative surgery patient comprising:
    a belt shaped to be worn about the abdomen, thorax, thigh or head of a wearer;
    a pocket having an internal cavity shaped to receive a surgical drainage receptacle, said pocket having a back panel, a front panel, and a gusset, said back panel made of a relatively non-abrasive material and having padding positioned therein such that pressure from a receptacle carried in said cavity is distributed about said back panel, said gusset being attached between said front panel and said back panel, said panels and said gusset forming said cavity, a hinge having a fixed end and a free end and forming a crotch attached to said front panel, said free end having a closure for releasably attaching said free end to said front panel wherein said fixed end of said hinge is positioned on said front panel below said free end of said hinge such that said crotch can support excess slack from a tube connected to a surgical drainage receptacle when said free end of said hinge is attached to said front panel, wherein said back panel also includes a loop for slidably receiving said belt, said loop being shaped to hold said pocket against said belt such that said belt is below an upper surface of said back panel, herein said pouch is held against a wearer such that a carried receptacle is held in a substantially upright position.

11. The support system of claim 10 wherein said gusset is made from a fabric having elastic properties.

12. The support system of claim 10 wherein said gusset is fabricated from a single piece of fabric.

13. The support system of claim 10 wherein said gusset is fabricated from two pieces of fabric, each of said pieces being attached between said front and back panels to form side panels.

14. The support system of claim 10 wherein said pocket includes a flap ending above said internal cavity having a releasable closure positioned thereon to releasably secure a corresponding flap on a drainage receptacle thereto, thereby providing additional support for said drainage receptacle.

15. The support system of claim 14 wherein said releasable closure is a snap.

16. A support device for use with a drainage receptacle connected to a postoperative surgery patient comprising:

a belt shaped to be worn about the abdomen of a wearer made of an elastic material having a non-abrasive surface, said belt having a plurality of loops attached in a spaced array to an end thereof, and complementary strips of hook and loop material attached to an opposite end of said belt, wherein said opposite end can be inserted though a selected one of said loops and can be folded over on itself to engage said strips of hook and loop material, thereby fastening said belt;

at least one pocket shaped to retain no more than a single mastectomy drainage bottle having an internal cavity, said pocket having a front panel, a back panel, and a gusset having upper edges positioned substantially evenly, said panels and said gusset defining said cavity and said edges defining a mouth for said cavity, a hinge having a fixed end and a free end and forming a crotch attached to said front panel, said free end having a closure for releasably attaching said free end to said front panel, wherein said fixed end of said hinge is positioned on said front panel below said free end of said hinge such that said crotch can support excess slack from a tube connected to a surgical drainage receptacle when said free end of said hinge is attached to said front panel, wherein said back panel further including a loop made of a relatively non-abrasive material having a top surface positioned substantially evenly with said panel upper edges for slidably receiving said belt, said loop being unitary with said back panel, and both said loop and said back panel having padding therein such that pressure from a receptacle carried in said cavity is distributed about said loop and said back panel, said loop shaped to hold said pocket against said belt such that said belt is below said upper edge of said back panel, wherein said pocket is held against a wearer such that a carried receptacle is held in a substantially upright position.

17. A method for supporting a post operative surgical drainage receptacle comprising the steps of:

selecting an adjustable belt shaped to be worn about the abdomen of a wearer;

selecting at least one pocket, said pocket having a front panel a back panel and a gusset made of a relatively non-abrasive material and having padding positioned therein such that pressure from a receptacle carried in said cavity is distributed about said back panel, a hinge having a fixed end and a free end and forming a crotch attached to said front panel, said free end having a closure for releasably attaching said free end to said front panel, wherein said fixed end of said hinge is positioned on said front panel below said free end of said hinge such that said crotch can support excess slack from a tube connected to a surgical drainage receptacle when said free end is attached to said front panel and said back panel also includes a loop for slidably receiving said belt, said loop being shaped to hold said pocket against said belt such that said belt is below an upper surface of said back panel, wherein said pocket is held against a wearer such that a carried receptacle is held in a substantially upright position;

slidably mounting said pocket on said belt;

fastening said belt around the abdomen of a post operative patient;

inserting a surgical drainage receptacle into said pocket; and gathering excess slack from a drainage tube attached to said drainage receptacle into a bundle, positioning said bundle in said crotch of said hinge and releasably closing said free end of said hinge to said front panel.

* * * * *